United States Patent
Floeder et al.

(10) Patent No.: US 7,023,542 B2
(45) Date of Patent: Apr. 4, 2006

(54) IMAGING METHOD AND APPARATUS

(75) Inventors: Steven P. Floeder, Shoreview, MN (US); James A. Masterman, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 369 days.

(21) Appl. No.: 10/115,533

(22) Filed: Apr. 3, 2002

(65) Prior Publication Data

US 2003/0189704 A1    Oct. 9, 2003

(51) Int. Cl.
*G01N 21/00*    (2006.01)

(52) U.S. Cl. .............. 356/239.1; 356/237.1; 356/397

(58) Field of Classification Search .. 356/239.1–239.3, 356/239.7, 239.8, 429–431; 250/214.1, 559.02, 250/559.11, 559.46
See application file for complete search history.

(56) References Cited

U.S. PATENT DOCUMENTS

| | | | |
|---|---|---|---|
| 3,330,178 A * | 7/1967 | Timson ...................... 73/157 |
| 3,338,130 A * | 8/1967 | Gaffard ...................... 356/431 |
| 3,788,750 A * | 1/1974 | Maltby et al. ............. 356/239.1 |
| 3,858,982 A * | 1/1975 | Meckler ...................... 356/127 |
| 4,310,242 A * | 1/1982 | Genco et al. ................ 356/128 |
| 4,634,281 A | 1/1987 | Eikmeyer |
| 4,737,650 A | 4/1988 | West |
| 4,775,238 A | 10/1988 | Weber |
| 4,797,558 A | 1/1989 | West |
| 4,812,039 A | 3/1989 | Shimada et al. |
| 4,938,601 A * | 7/1990 | Weber ........................ 356/429 |
| 5,047,640 A * | 9/1991 | Brunnschweiler et al. ....................... 250/341.8 |
| 5,452,079 A | 9/1995 | Okugawa |
| 5,515,158 A | 5/1996 | Heineck |
| 5,559,341 A | 9/1996 | Krasinski et al. |
| 5,642,198 A | 6/1997 | Long |
| 5,691,811 A * | 11/1997 | Kihira ...................... 356/239.1 |
| 5,745,236 A | 4/1998 | Haga |
| 6,075,591 A * | 6/2000 | Vokhmin ................. 356/239.1 |
| 6,181,416 B1 | 1/2001 | Falk |
| 6,260,974 B1 | 7/2001 | Koyama |

FOREIGN PATENT DOCUMENTS

| | | |
|---|---|---|
| DE | 39 26 349 | 2/1991 |
| DE | 41 39 094 | 6/1993 |
| JP | 08 327561 | 12/1996 |
| SU | 840 712 | 6/1981 |
| WO | WO 87/07383 | 12/1987 |
| WO | WO 01/81904 A1 | 11/2001 |
| WO | WO 02/12869 A1 | 2/2002 |

OTHER PUBLICATIONS

G.w.Neudeck et al., Precision Crystal corner cube arays for optical grating, formed by (100) silicon planes with selective epitaxial growth, App. Opt. 35, pp. 3466-3470, 1996.*

(Continued)

*Primary Examiner*—Hoa Q. Pham
(74) *Attorney, Agent, or Firm*—Brian E. Szymanski

(57) ABSTRACT

The present invention relates to imaging apparatus and method for detecting optical properties of transparent media. The present invention superimposes, either optically or electronically, at least two images of the transparent media in order to obtain the optical properties. By superimposing the images, the present invention is capable of detecting various optical properties of the transparent medium in a single configuration.

47 Claims, 5 Drawing Sheets

OTHER PUBLICATIONS

*Optics*. Hecht-Zajac. Addison-Wesley Series in Physics. 1974. pp 478-480.

*Scientific American*. "The Amateur Scientist", Jearl Walker, pp. 118-123.

* cited by examiner

IMAGING METHOD AND APPARATUS

TECHNICAL FIELD

The present invention relates to an imaging method and apparatus ideally suited for analyzing the optical quality of at least a portion of a transparent medium, more particularly the invention superimposing multiple images to analyze the quality of a transparent medium, for example, to detect refracting, obstructing and scattering defects.

BACKGROUND OF THE INVENTION

An undesirable result in the manufacture of transparent films, such as optical films, is the occurrence of either functional or cosmetic defects in the film. There are numerous potential causes of these defects and they generally manifest themselves in different manners. For example, for transparent and semi-transparent films, surface scratches may scatter light, caliper variations may cause slight refractive variations, and debris may block transmitted light or scatter reflective light. Because of the subtle nature of defects, the small size of the defects, and variety of defects, it is difficult to manually inspect outgoing film to ensure quality.

Various attempts have been made to automatically inspect optical films, thereby improving defect detection capabilities and reducing costs when compared to manual inspection. While some have been successful, one difficult issue has been the inability of automated systems to detect caliper change defects that manifest themselves as subtle flow patterns in the film. Further, the detection of different types of defects generally requires more than a single optical configuration. For example, to detect scratches, flow patterns, and debris may require two or three optical configurations along with associated processing electronics.

Conventionally practiced web inspection systems generally incorporate line scan cameras that are capable of detecting scattering defects such as scratches or surface particles. The line scan cameras are configured with dark-field optics in either reflected or transmitted mode and are capable of detecting the noted defects. However, this single configuration is not sufficient for detecting refracting defects or embedded particles that do not distort the surface of film.

Laser scanners can be configured with multiple channels in order to be sensitive to all defects at the same time. Basically, this is the same as having multiple systems, one for each channel, which increases the system complexity and cost. Also, laser scanners are large, complex electromechanical systems that are expensive to implement in production environments. Laser scanners are also difficult to run in parallel for inspection applications requiring extremely high resolution across wide webs.

Another imaging technique is referred to as schlieren imaging. This technique is generally useful for measuring variations in the refractive index within an optical system. The technique detects inhomogeneities within a medium by detecting the energy refracted by that portion of the medium in which the inhomogeneity occurs. Schlieren imaging is generally used over long distances with large objects. The system is not suitable for film inspection because it is only capable if detecting changes in the refractive index of the medium.

It would be advantageous to provide a single imaging method and device capable of detecting and quantifying different optical properties of transparent films. It would also be an advantage to detect refracting, obstructing and scattering defects with a single imaging configuration.

SUMMARY OF THE INVENTION

The present invention is directed to an imaging apparatus and method for detecting anomalies and quantifying optical properties of transparent media. The present invention superimposes, either optically or electronically, at least two images of the transparent media in order to obtain optical properties of at a least a portion of the transparent medium.

In one embodiment, the method for characterizing the optical properties of a transparent media includes transmitting light from a point light source two times through the transparent medium. The light is directed through a lens onto a detector array to form an image of the transparent medium. At least one converging mirror is utilized to direct light to a point at a position substantially near the optical center of the lens. The image is then analyzed using conventional analytical techniques to characterize the optical properties of the transparent medium. Preferably, the combined distance between the point light source to the converging mirror and from the converging mirror to the detector array is about four times the focal length of the mirror.

In another embodiment, a method for characterizing transparent media involves superimposing two or more images of a transparent medium wherein each image is generated by reflecting light emitted from a point light source off a converging mirror. The light converges to a single point substantially near the center of a lens. The light is transmitted through the transparent medium either before or after reflecting from the mirror. Two or more images are formed, each having unique focal planes, such that one of the unique focal planes corresponds to the transparent medium. The images may be superimposed through the use of a single lens onto a detector array. Alternatively, the images may be formed using two or more lenses with separate detector arrays, and the corresponding signals from the detector arrays superimposed electronically.

The apparatus of the present invention generally includes a point light source for transmitting light through a transparent medium. A converging mirror is provided for reflecting the light back through the transparent medium to a point at a position substantially near the optical center of the lens. A detector array receives an image from the lens. The image is analyzed in an analyzing device to determine optical properties of said transparent medium.

A preferred embodiment of the apparatus of the present invention superimposes two or more images of a transparent medium. The apparatus includes one or more imaging systems. Each system has a point light source for transmitting light through a transparent medium and a converging mirror positioned such that light from the point light source converges to a point substantially near a center of an imaging lens. A detector array is included in the apparatus for receiving an image from the lens. Each system generates an image and each image has unique focal planes, such that one of the unique focal planes corresponds to the transparent medium.

The embodiments of the present invention are capable of characterizing optical characteristics in the transparent medium such as, for example, defects, non-uniformities, and variations in clarity, optical density, or diffusion. Preferably, the method of the present invention is capable of detecting optical defects including refracting defects, scattering defects, and obstructing defects with a single configuration.

For purposes of the present invention, the following terms used in this application are defined as follows:

"web" means a sheet of material having a dimensional width in one direction and indeterminate length in the orthogonal direction;

"converging mirror" means a mirror configured specifically such that light emitted from a single point is directed back to a single point after reflection from the mirror surface;

"imaged line on web" means a portion of the web which is currently being imaged onto the detector array;

"point light source" means a source of electromagnetic radiation with the physical form of a single point;

"beamsplitter" means an optical device that uses a mirror or prisms to divide a light beam into two or more paths;

"lens" means an object or group of objects that bend light rays causing them to converge or diverge to create an image;

"camera" means a wide variety of devices through which light from an object is focused onto a light-sensitive material, such as film or semiconductor devices, in order to record the image; and "detector array" means an array of photosensitive devices capable of converting incoming light photons into an electrical signal.

BRIEF DESCRIPTION OF THE DRAWINGS

The advantages of the present invention will become readily apparent to those skilled in the art from the following detailed description when considered in the light of the accompanying drawings in which.

While the above-identified drawing figures set forth one embodiment of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION

The present invention is suitable for determining optical properties of a transparent medium. The invention provides mechanisms for superimposing two or more images of at least a portion of the transparent medium. The images are superimposed either optically or electronically in order to determine the optical characteristics of the transparent medium.

Figure 1:
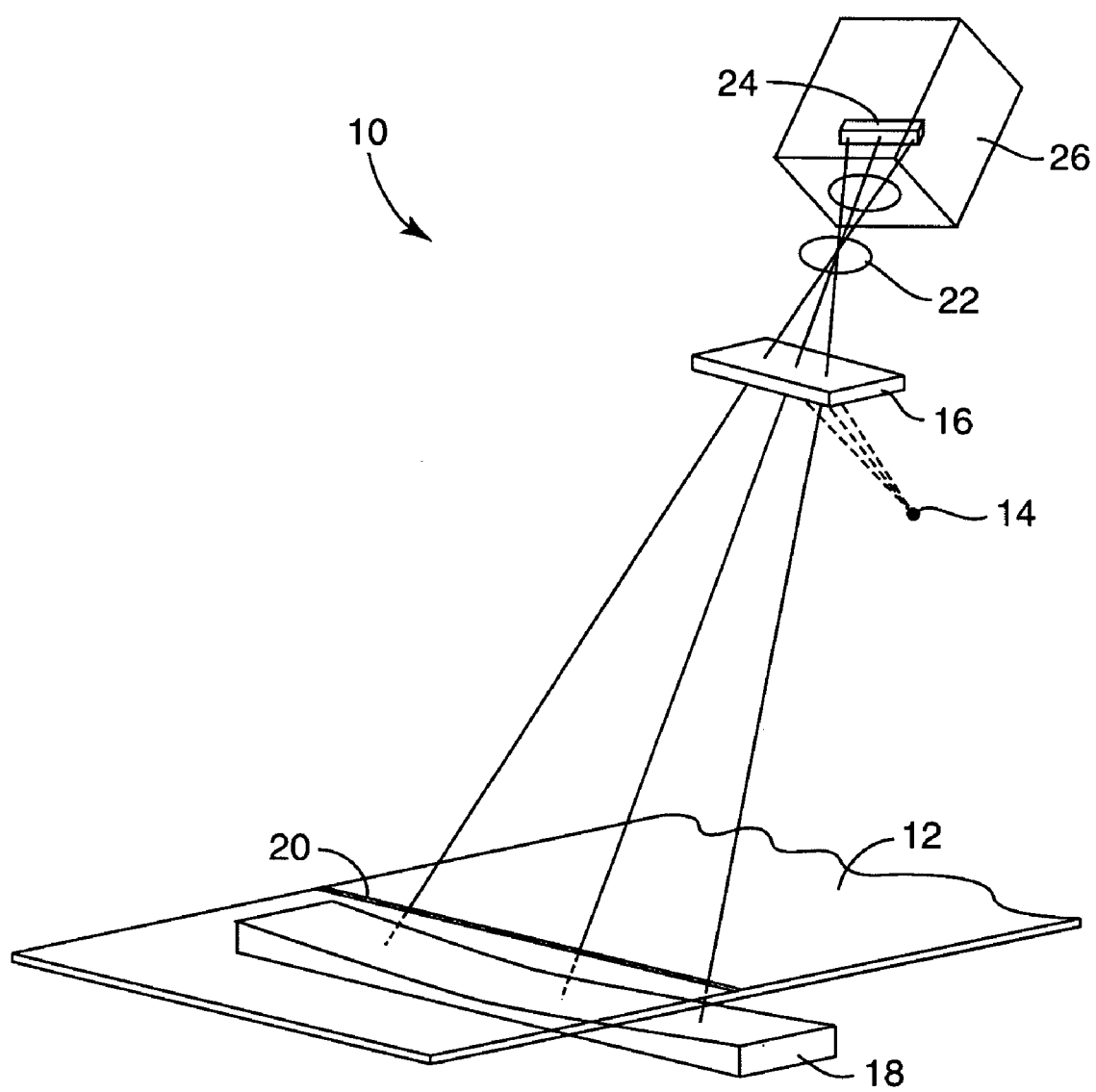
FIG. 1 is an isometric view of one embodiment of the present invention.

FIG. 1 depicts one embodiment of the apparatus and method of the present invention. In general, the imaging system 10 is suitable for imaging optical properties of a transparent medium 12. The imaging system 10 includes a point light source 14 that directs light onto beam splitter 16. The light is transmitted through the transparent medium 12 and onto a converging mirror 18. The light is then reflected back through the transparent medium 12 through the same line or area as the first pass of light. This line or area is referred to as the imaged area 20. The light reflected from the converging mirror and passing through the imaged area 20 for the second time is directed to the lens 22. The light from the converging mirror 18 is directed to a point on the lens 22 at a position substantially near the optical center of lens 22. A detector array 24, residing in camera 26, receives the light from the lens and forms electrical signals corresponding to the imaged area 20 of transparent medium 12. The electrical signals from the detector array representing the image of transparent medium may then be processed or analyzed using conventionally recognized techniques.

Figure 2:
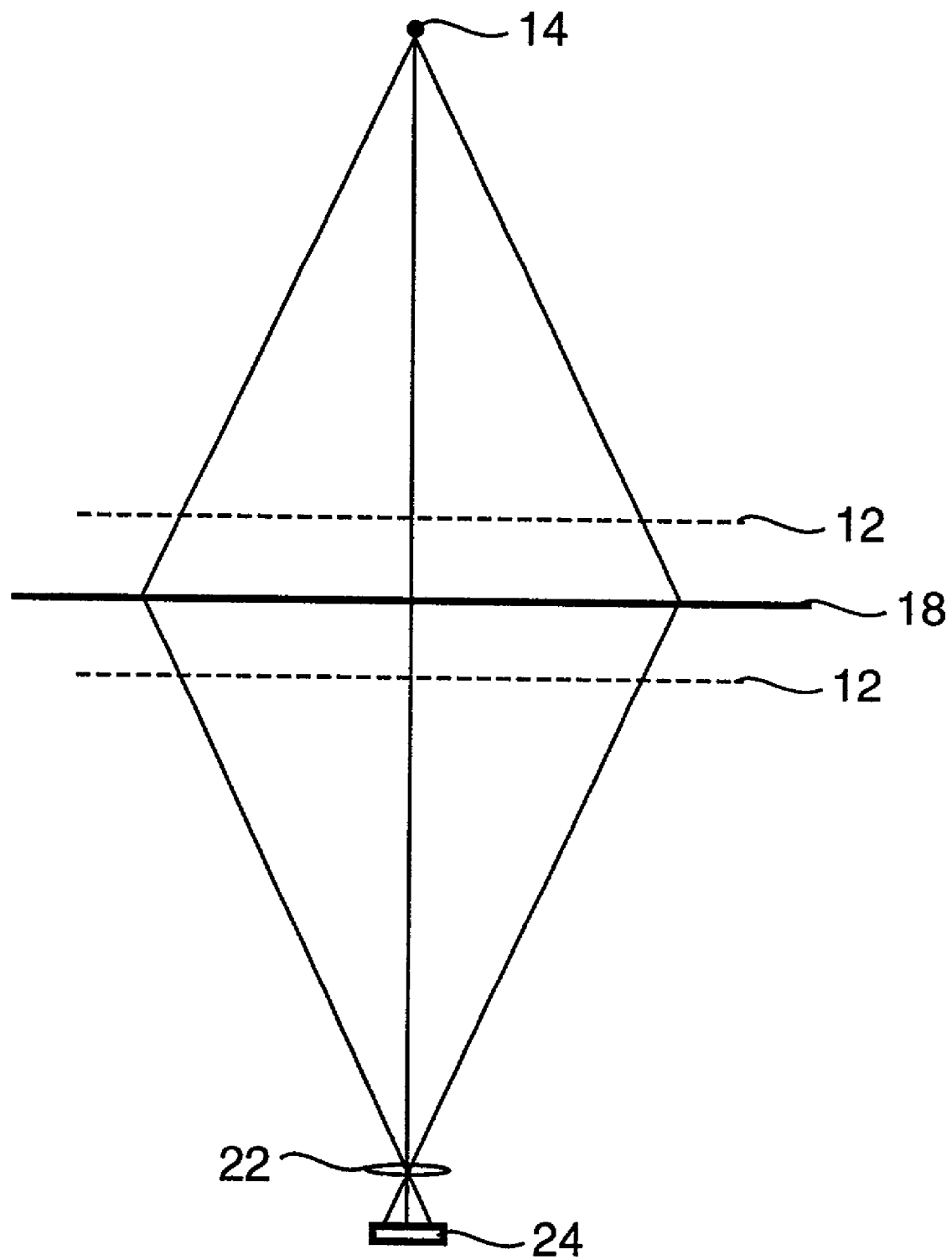
FIG. 2 is an isometric view of the embodiment of FIG. 1 in an unfolded array.

FIG. 2 is provided to further illustrate, in an unfolded view, the embodiment of FIG. 1. The light from point light source 14 fans out from the point light source 14 and through the transparent medium 12 until it reflects from the converging mirror 18. The reflected light passes back through web 12 for a second time and converges to a single point. In accordance with the present invention, the point at which the light converges after reflecting from the converging mirror 18 is a point substantially near the optical center of lens 22. An image of the web is provided by the detector array 24 from the light passing through the lens 22.

The present invention is suitable for imaging optical properties of a transparent medium. A transparent medium may be any material that is capable of allowing at least some transmission of light with no appreciable scattering or diffusion. Preferably, the transparent medium is selected from polymeric films, glass, coated films or coated glass. The transparent medium may be preferably provided in either web form or as discrete parts. In the case of web imaging, the web may be traveling at a predetermined speed while the present invention is providing images of continuous segments or an imaged area of the web as the web travels through the area highlighted by the point light source.

In the manufacture of transparent media, such as films, it is generally desirable that the medium's optical properties be substantially uniform. Unfortunately, the manufacturing process may introduce undesirable optical properties in the transparent medium. For example, optical properties of the transparent medium may involve such characteristics as defects, caliper, non-uniformities, clarity, optical density, diffusion or combinations of these noted characteristics. The present invention is capable of imaging the transparent medium to determine variations of one or all of the noted properties from a desired standard.

Conventional imaging systems are not capable of addressing various types of defects in a single configuration. For example, conventional configurations are not capable of detecting refracting defects while simultaneously detecting other defects such as scattering defects or obstructing defects. The ability of the present invention to simultaneously image at least two views of the same section of imaged medium enables inspection of the medium for such optical properties as refracting defects, scattering defects, obstructing defects or combinations thereof in a single configuration.

In accordance with the present invention, a point light source is utilized to transmit electromagnetic radiation. The point light source is selected to provide sufficient energy so that the detector array records an image of the transparent medium. Those skilled in the art are capable of selecting a point light source to match specific detector arrays. All conventionally recognized point light sources are suitable for use with the present invention. Non-limiting examples of point light sources may include incandescent lamps, fiber optic light or light emitting diodes. In a preferred embodiment, an aperture may be used to limit the effective size of the source. Typical aperture sizes range from 100 μm to 5 mm.

In a preferred embodiment, a beam splitter is utilized to divide a light beam into two or more paths. Beam splitters may be employed in various alignments to provide coaxial lighting. Coaxial lighting may assist in reducing the occurrence of single features represented twice on a single image, also referred to as ghosting. Conventional beam splitters are suitable for use with the present invention.

A converging mirror, employed in practicing the present invention, is configured specifically such that light emitted from the point light source is directed back to a point after reflecting from the mirror surface. Preferably, the converging mirror directs light to a point at a position near the optical center of the lens. The converging mirror may be converging in at least one dimension and preferably two dimensions. The type of converging mirror employed affects the imaging system's sensitivity. Certain forms of transparent media and specific types of optical properties require higher quality mirrors in order to appropriately image specific optical properties. Those skilled in the art are capable of matching mirror quality to achieve the level of imaging needed for specific transparent films.

In an optional embodiment, the present invention may also employ flat mirrors to fold the optical path, thereby drastically reducing physical space requirements for the inventive apparatus.

A lens is employed in the method and apparatus of the present invention. The lens bends light rays, causing them to converge and create an image on the detector array. It serves to map a physical section of the transparent media to corresponding positions on the detector array. The lens is preferably focused on a plane corresponding to the position of the transparent medium.

The detector array is an array of photosensitive devices capable of converting incoming light photons into electrical signals. The lens forms an image on the detector array. The detector array converts image intensity to corresponding electrical signal amplitude. The signal created by the detector array is an electronic representation of the optical image transmitted by the lens. Conventional detector arrays generally recognized by those skilled in the art are suitable for use with the present invention. Preferably, acceptable detector arrays may include either one-dimensional or two-dimensional arrays of a charge coupled device (CCD), a complimentary metal oxide semiconductor (CMOS) or photodiodes.

The operation of the present invention is described with further reference to the embodiment of FIG. 1. The configuration of imaging system 10 is set up so that the combined distance from point light source 14 to converging mirror 18 and from the mirror to a convergence point near the center of lens 22 are about equal to four times the mirror's 18 focal length. FIG. 2 shows the two light paths unfolded. Typically, the distance from the point light source 14 to the mirror 18 is equal to the distance from the mirror 18 to the center of the lens 22. However, the distances may be slightly unequal while still maintaining good convergence as long as the total distance remains substantially close to four times the mirror's 18 focal distance.

When aligning the optical components, it is useful to use a laser diode in place of the point light source 14. A typical alignment procedure with the preferred embodiment is as follows. First, roughly align the beamsplitter 16, converging mirror 18, lens 22, and camera 26 using conventional methods such that the center of the camera 26, lens 22, beamsplitter 16, and converging mirror 18 are coaxial. Also, position the point light source 14 and lens 22 so that the total distance between them is 4F as described above. Next, using the laser in place of the point light source 14, fine-tune the beamsplitter 16 position until the beam exactly impacts the mirror's 18 center. Next, adjust the mirror 18 such that the laser beam travels back through the center of the beamsplitter 16. Next, adjust the camera 26 such that the laser impacts the center of the detecting array 24. At this point, replace the laser with the point light source 14 and adjust the lens 22 position, forward or backward, so that the light converges substantially near the lens 22 center. Finally, adjust the camera's 26 position forward and backward until the detecting array 24 is fully illuminated by the light as it diverges from the point. It may be necessary to iterate this process until the optical system is fully aligned. If the system is not aligned properly, it may result in the loss of optical signal fidelity.

In the embodiment depicted in FIGS. 1 and 2, only a single converging mirror 18 is used. Therefore, the light may impact the transparent medium 12 at slightly different angles depending on the cross-medium position. However, depending of the composition of the transparent medium 12, it may be necessary to ensure that all light impacts the transparent medium 12 in exactly the same manner regardless of position.

Figure 3:
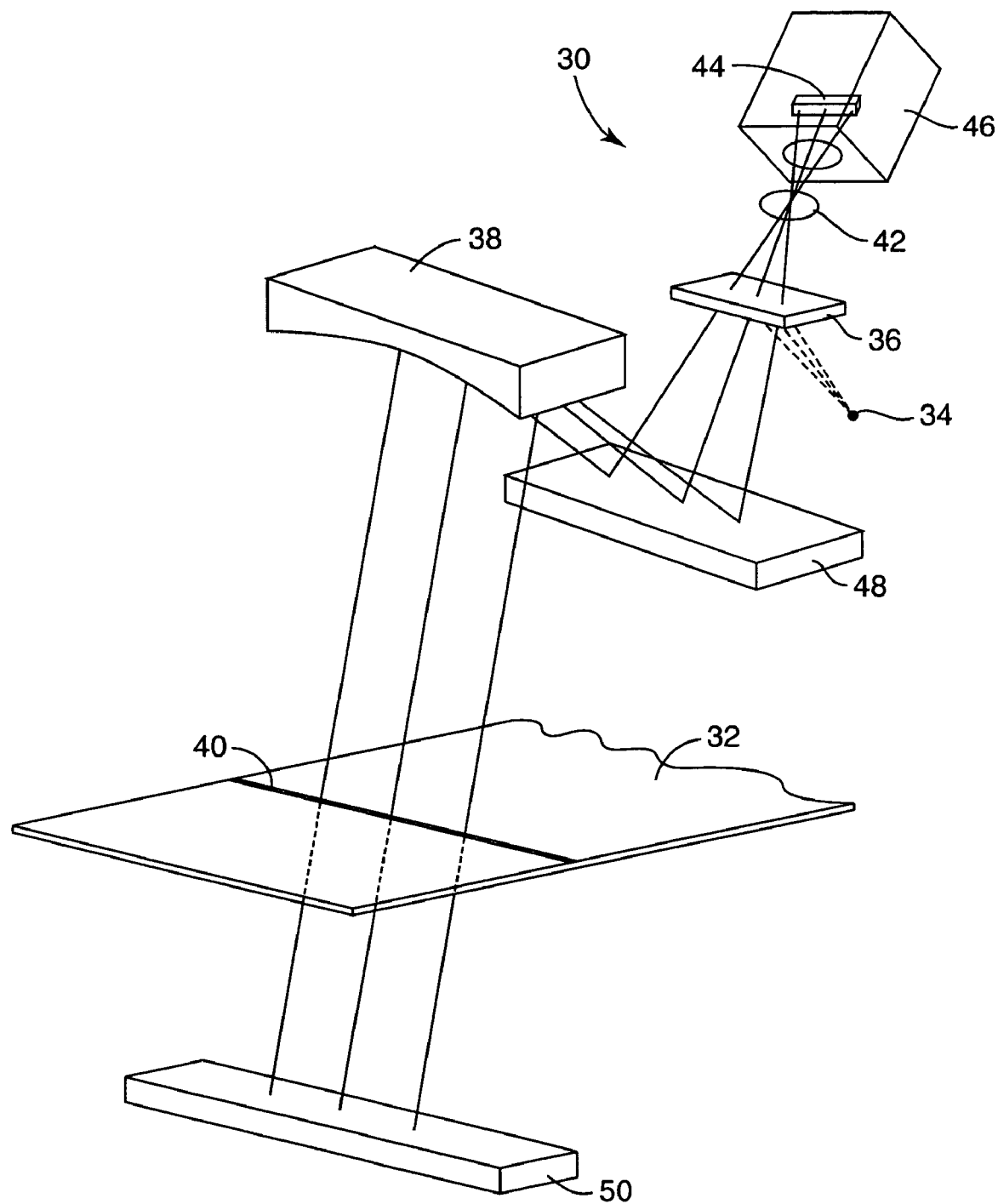
FIG. 3 is an isometric view of another embodiment of the present invention.

An alternative embodiment is illustrated in FIG. 3. The imaging system 30 is set up to image the optical properties of transparent medium 32. In this case, the point light source 34 is positioned relative to the converging mirror 38 such that all light rays will be reflected in parallel. This is referred to as telecentric imaging. The point light source emits light through beam splitter 36. The light is transmitted to flat mirror 48 where it is directed to converging mirror 38. The converging mirror 38 reflects the light in parallel through transparent medium 32 to create an imaged area 40. The light reflects from a second flat mirror 50 and is transmitted back through transparent medium 32, reflected from converging mirror 38 and flat mirror 48 to lens 42. The lens 42 provides an optical image that is then converted to electrical signals in a detector array 44 which resides in camera 46. FIG. 3 exemplifies the situation where the light rays, when placed at the focal point of a parabolic mirror, impacts the web in exactly the same manner, are reflected from flat mirror, and travel back to the converging mirror where they are again converged to a single point in the center of the imaging lens.

The imaging resolution with this embodiment depicted in FIG. 3 is highly dependent on the specific implementation. Typical resolutions useful for web or piece part inspection may range from 20 μm to 1 mm as imaged on the detector array. However, the method is capable at resolutions as low as 100 mm or as high as 1 μm. The only limitations are the size and accuracy of the converging mirror combined with the number of pixels and sensitivity of the sensor array.

Figure 4A:
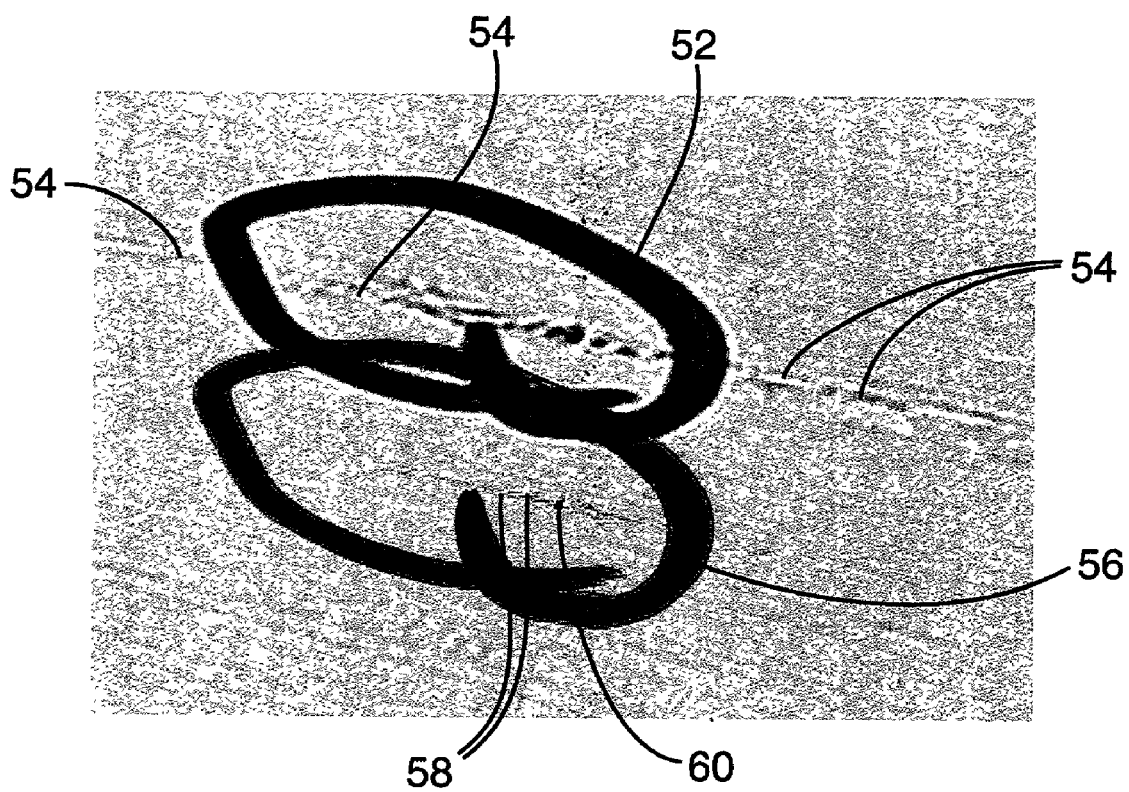
FIGS. 4a, and 4b are images of a various types of defects that may be detected through use of the present invention.

The image resulting from preferred embodiments actually consist of two superimposed images, one from each light pass through the transparent medium. As shown in FIG. 2, the imaging plane of lens 14 is usually equal to the plane of the second pass. Thus, the first pass through the transparent medium 12 will not be in focus relative to the lens 22. The image depicted in FIG. 4a shows the relative contributions from each of the two passes. The first pass 52 accentuates subtle refracting defects 54 and is most effective if it is out of focus. The second pass 56 is then most sensitive to the light scattering 58 or obstructing defects 60.

Figure 4B:
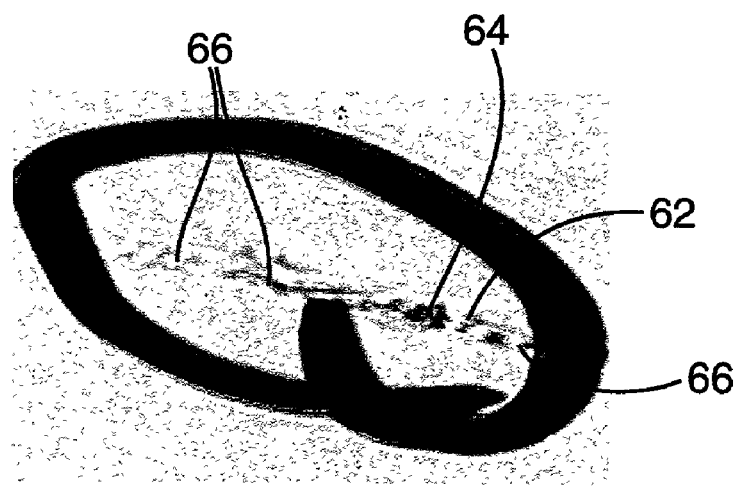

By superimposing two images through alignment of the two imaging passes, those skilled in the art can realize the benefits of the two individual images in a single image, thereby simplifying the image processing and maintaining positional accuracy for interpretation of the optical properties of the transparent medium. The image depicted in FIG. 4*b* shows a superposition of the two passes described in FIG. 4*a*. It effectively captures the high frequency components related to small scattering defects 62 or obstructing defects 64, such as scratches and particles, while also providing a strong optical signature for subtle refracting defects 66 such as polymer flows or caliper variations.

After an image is captured, it must be analyzed to provide information about the optical properties of the transparent medium, such as, for example, defects. There are a variety of conventional methods to process the image to extract process variations. For defect detection, possible methods include, but are not limited to, spatial or frequency based filtering to enhance the defects followed by intensity level thresholding to binarize the image. After binarization, conventional blob analysis can be performed to extract and analyze the defects. For uniformity analysis, many different statistical analyses can be performed to quantify the variability of the image and thereby quantify the manufacturing process variability. As the process variability or defect level is quantified through this imaging technique, the results can then be used to improve and control the manufacturing process to increase and maintain high quality levels.

Figure 5:
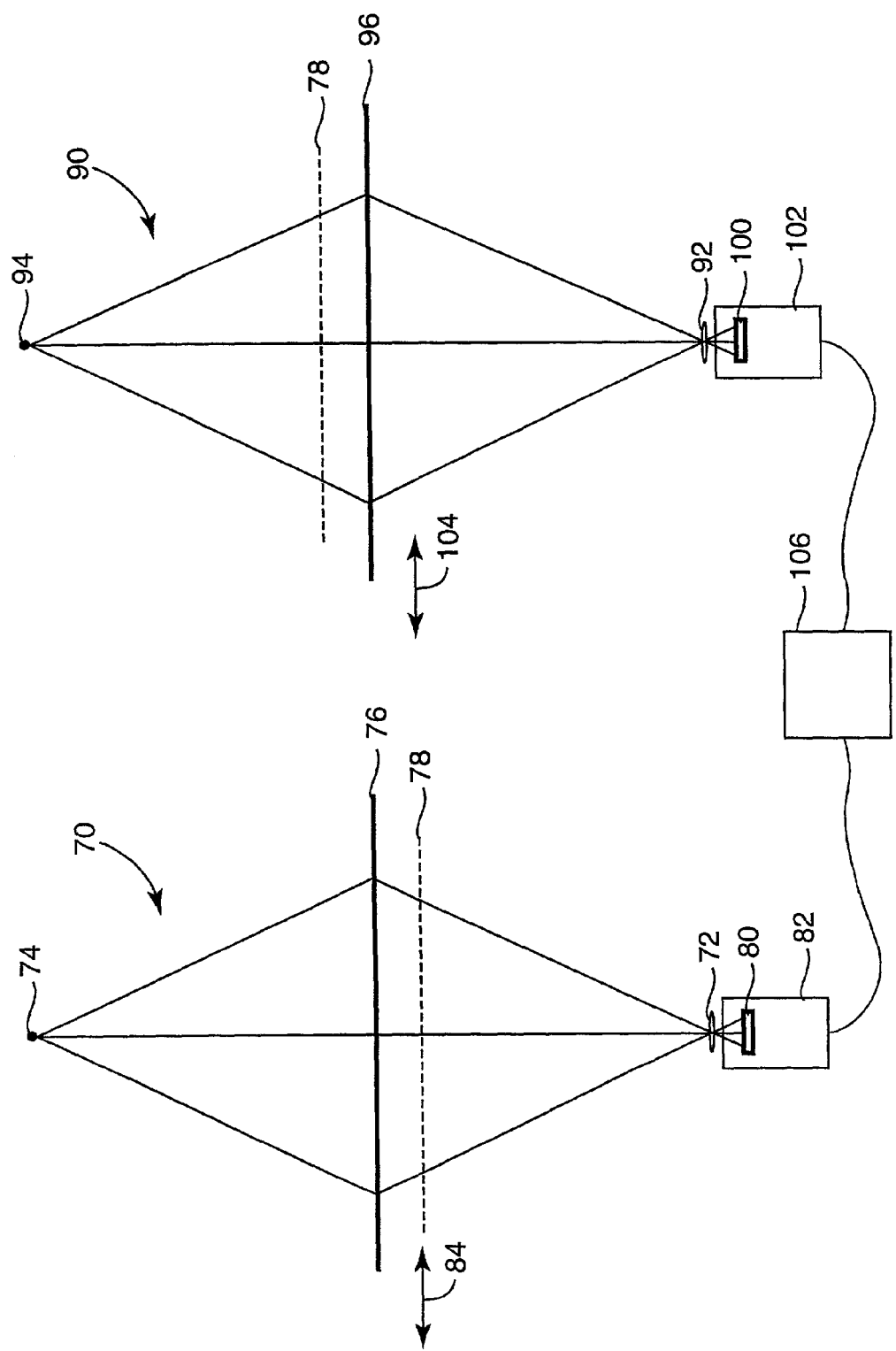
FIG. 5 is an isometric view of an alternative embodiment of the present invention.

In an alternative embodiment, the images of the transparent medium may be superimposed electronically as opposed to optically. There are numerous alternative embodiments capable of producing similar benefits through the combination of independent single pass imaging systems. One such embodiment is shown in FIG. 5. In this case, the first system 70 uses the focused lighting with the lens 72 focused in the plane of transparent medium 78. The focal plane of lens 72 is depicted by arrow 84. This corresponds to the second pass from the preferred embodiment. The point light source 74 is directed to a converging mirror 76. The light is reflected from the converging mirror 76 through transparent medium 78. The light passing through transparent medium 78 is directed to a point on the lens 72 substantially near the optical center of the lens 72. This provides a first image on a detector array 80 located in camera 82.

The second system 90 uses the focused lighting from with the lens 92 focused before the plane of transparent medium 78 and corresponds to the first pass from the preferred embodiment. The focal plane of lens 92 is depicted by arrow 104. The point light source 94 is directed through transparent medium 78 to a converging mirror 96. The light is reflected from the converging mirror 96 to a point on the lens 92 substantially near the optical center of the lens 92. This provides a second image on a detector array 100 located in camera 102.

The image output from the two detector arrays 80, 100 are then superimposed electronically in a combining device 106. Non-limiting examples of combining devices include computers with multiple digital input channels or dedicated dyadic image processing hardware. The superimposed image of the optical characteristics of the transparent medium 78 may then be processed similar to that described in the preferred embodiment. Alternative embodiments such as that described with respect to FIG. 5 provide a desired level of flexibility because two or more imaging systems can be separately configured to enhance desired features.

From the above disclosure of the general principles of the present invention and the preceding detailed description, those skilled in this art will readily comprehend the various modifications to which the present invention is susceptible. Therefore, the scope of the invention should be limited only by the following claims and equivalents thereof.

What is claimed is:

1. A method for characterizing a transparent medium, comprising
   (a) transmitting light from a point light source two times through said transparent medium and then through a lens onto a detector array to form a superposition of two or more images of said transparent medium, wherein at least one converging mirror directs light to a point at a position substantially near the optical center of the lens, and wherein the focal plane for one of the images corresponds to the transparent medium; and
   (b) analyzing said image to characterize optical properties of said transparent medium.

2. A method according to claim 1, wherein said optical properties include defects, caliper, non-uniformities, clarity, optical density, diffusion or combinations thereof.

3. A method according to claim 2, wherein defects include refracting defects, scattering defects, obstructing defects or combinations thereof.

4. A method according to claim 1, wherein the combined distance between the point light source to the converging mirror and from the converging mirror to the detector array is about four times the focal length of the mirror.

5. A method according to claim 1, wherein a beam splitter is utilized to align light so that a first pass of light from said point light source through said transparent medium is co-axial with a second pass of light from said mirror through said transparent medium.

6. A method according to claim 1, wherein said point light source is selected from apertured lamps, fiber optic light or light emitting diodes.

7. A method according to claim 1, wherein said transparent medium is polymeric films, glass, coated films or coated glass.

8. A method according to claim 1, wherein the detector array is one-dimensional or two-dimensional.

9. A method according to claim 1, wherein said image is analyzed using filtering, blob analysis, thresholding or combinations thereof.

10. A method according to claim 1, further comprising identifying locations of one or more defects on said transparent medium.

11. A method according to claim 1, further comprising quantifying optical properties of said transparent medium.

12. A method according to claim 1, wherein said transparent medium includes webs or discrete parts.

13. A method according to claim 1, wherein said defects are one micron or greater.

14. A method according to claim 1, wherein said detector arrays include CCD, CMOS, or photodiodes.

15. A method according to claim 1, further comprising adjusting processing of said transparent medium based on said optical properties.

16. A method according to claim 1, wherein said light impacts said transparent medium in a telecentric manner.

17. A method for characterizing a transparent medium, comprising
   (a) passing light from a point light source through said transparent medium onto a converging mirror;
   (b) reflecting light from said converging mirror back through said transparent medium and through a lens onto a detector array to form a superposition of two or more images of said transparent medium, wherein light from said mirror converges to a point at a position substantially near the optical center of the lens, and wherein a focal plane for one of the images corresponds to the transparent medium; and (c) analyzing said image to characterize optical properties of said transparent medium.

18. A method of characterizing a transparent medium, comprising, superimposing two or more images of a transparent medium wherein each image is generated by reflecting light emitted from a point light source from a converging mirror such that the light converges to a single point substantially near the center of a lens with said light transmitting through said transparent medium either before or after reflecting from the mirror, wherein the lens is focused on a plane corresponding to the transparent medium, and wherein the two or more images are formed, each having unique focal planes, such that one of the unique focal planes corresponds to the transparent medium.

19. A method according to claim 18, wherein, the images are superimposed through a single lens onto a detector array.

20. A method according to claim 18, wherein, the images are formed using two or more lenses with separate detector arrays, and signals from said detector arrays are superimposed electronically.

21. A method according to claim 18, further comprising analyzing said superimposed image to characterize optical properties of said transparent medium.

22. A method according to claim 21, wherein said optical properties include defects, caliper, non-uniformities, clarity, optical density, diffusion or combinations thereof.

23. A method according to claim 22, wherein defects include refracting defects, scattering defects, obstructing defects or combinations thereof.

24. A method according to claim 1, wherein said image is analyzed using filtering, blob analysis, thresholding or combinations thereof.

25. A method according to claim 21, further comprising quantifying optical properties of said transparent medium.

26. A method according to claim 18, further comprising adjusting processing of said transparent medium based on said optical properties.

27. An apparatus for detecting optical characteristics in a transparent medium, comprising
(a) a point light source for transmitting light through said transparent medium;
(b) a converging mirror for reflecting said light back through said transparent medium and to a point at a position substantially near the optical center of a lens, wherein;
(c) a detector array for receiving an image from said lens that represents a superposition of two or more images of said transparent medium and wherein a focal plane for one image corresponds to the transparent medium; and
(d) an analyzing device for analyzing said image to determine optical properties of said transparent medium.

28. An apparatus according to claim 27, wherein said optical properties include defects, caliper, non-uniformities, clarity, optical density, diffusion or combinations thereof.

29. An apparatus according to claim 28, wherein said defects include refracting defects, scattering defects, obstructing defects or combinations thereof.

30. An apparatus according to claim 28, wherein said defects are one micron or greater.

31. An apparatus according to claim 29, further comprising processing said transparent medium based on said defects.

32. An apparatus according to claim 27, wherein the combined distance between the point light source to the converging mirror and from the converging mirror to the detector array is about four times the focal length of the mirror.

33. An apparatus according to claim 27 further comprising a beam splitter to align the light so that a first pass of light from said point light source through said transparent medium is co-axial with a second pass of light from said mirror through said transparent medium.

34. An apparatus according to claim 27, wherein said point light source includes apertured lamps, fiber optic light or light emitting diodes.

35. An apparatus according to claim 27, wherein said transparent medium is polymeric films, glass, coated films or coated glass.

36. An apparatus according to claim 27, wherein the detector array is one-dimensional or two-dimensional.

37. An apparatus according to claim 27, wherein said image is analyzed using filtering, blob analysis, thresholding or combinations thereof.

38. An apparatus according to claim 27, wherein said analyzing device identifies locations of one or more defects on said transparent medium.

39. An apparatus according to claim 27, wherein said transparent medium includes webs or discrete parts.

40. An apparatus according to claim 27, wherein said detector arrays include CCD, CMOS, or photodiodes.

41. An apparatus according to claim 27, wherein said light impacts said transparent medium in a telecentric manner.

42. An apparatus for superimposing two or more images of a transparent medium, comprising:
two or more imaging systems, each system having a point light source for transmitting light through a transparent medium, a converging mirror positioned such that light from the point light source converges to a point substantially near a center of an imaging lens, wherein the lens is focused on a plane corresponding to the transparent mediums and a detector array for receiving an image from said lens, wherein each system generates an image, each image having unique focal planes, such that one of the unique focal planes corresponds to the transparent medium.

43. An apparatus according to claim 42, wherein, the images are superimposed through a single lens onto a detector array.

44. An apparatus according to claim 42, wherein, the images are formed using two or more lenses with separate detector arrays, and signals from said detector arrays are superimposed electronically.

45. An apparatus according to claim 42, wherein said optical properties include defects, caliper, non-uniformities, clarity, optical density, diffusion or combinations thereof.

46. An apparatus according to claim 42, wherein defects include refracting defects, scattering defects, obstructing defects or combinations thereof.

47. An apparatus according to claim 42, wherein said image is analyzed using filtering, blob analysis, thresholding or combinations thereof.

* * * * *